(12) United States Patent
Zhang

(10) Patent No.: US 9,949,682 B2
(45) Date of Patent: Apr. 24, 2018

(54) METHOD FOR DETERMINING TARGET OF ALCOHOL TEST, DRIVING SAFETY DEVICE AND SYSTEM, SERVER

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventor: Xuebo Zhang, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

( * ) Notice: Subject to any disclaimer, the term of this patent is extended or adjusted under 35 U.S.C. 154(b) by 0 days.

(21) Appl. No.: 15/328,801

(22) PCT Filed: Mar. 29, 2016

(86) PCT No.: PCT/CN2016/077635
§ 371 (c)(1),
(2) Date: Jan. 24, 2017

(87) PCT Pub. No.: WO2017/041482
PCT Pub. Date: Mar. 16, 2017

(65) Prior Publication Data
US 2017/0215783 A1    Aug. 3, 2017

(30) Foreign Application Priority Data

Sep. 8, 2015   (CN) .......................... 2015 1 0566254

(51) Int. Cl.
*G08B 23/00*   (2006.01)
*A61B 5/18*    (2006.01)
(Continued)

(52) U.S. Cl.
CPC .............. *A61B 5/18* (2013.01); *A61B 5/0075* (2013.01); *A61B 5/4845* (2013.01);
(Continued)

(58) Field of Classification Search
CPC combination set(s) only.
See application file for complete search history.

(56) References Cited

U.S. PATENT DOCUMENTS

2003/0120139 A1\* 6/2003 Duval ...................... A61B 5/18
                                                      600/363
2007/0296601 A1\* 12/2007 Sultan ..................... A61B 5/18
                                                      340/576
(Continued)

FOREIGN PATENT DOCUMENTS

CN   101178831 A   5/2008
CN   104228579 A   12/2014
(Continued)

OTHER PUBLICATIONS

International Search Report dated Jul. 5, 2016 issued in corresponding International Application No. PCT/CN2016/077635.
(Continued)

*Primary Examiner* — Travis Hunnings
(74) *Attorney, Agent, or Firm* — Nath, Goldberg & Meyer; Joshia B. Goldberg; Annie Kock

(57) ABSTRACT

The present invention provides a method for determining a target of alcohol test, including: determining whether a motor vehicle satisfies a preset condition; and determining, as a target vehicle, a motor vehicle that satisfies at least one preset condition. The preset condition comprises at least one of: a parking duration in an area, in which a distance from a place selling alcoholic drinks does not exceed a predetermined distance, has a value within a predetermined range; alcohol content in a body of a driver of the motor vehicle exceeds a predetermined value; and schedule of a driver of the motor vehicle on that driving day comprises having a meal and/or a dinner party. The present invention further provides a driving safety device, a server and a driving safety system.

14 Claims, 2 Drawing Sheets

(51) Int. Cl.
 G08G 1/01 (2006.01)
 G07C 5/00 (2006.01)
 A61B 5/00 (2006.01)

(52) U.S. Cl.
 CPC .......... *A61B 5/6893* (2013.01); *A61B 5/7282* (2013.01); *A61B 5/746* (2013.01); *G07C 5/008* (2013.01); *G08G 1/01* (2013.01)

(56) References Cited

U.S. PATENT DOCUMENTS

| | | | | |
|---|---|---|---|---|
| 2011/0213628 A1* | 9/2011 | Peak | ...................... | G06Q 40/08 |
| | | | | 705/4 |
| 2012/0299713 A1* | 11/2012 | Elia | ................... | B60W 30/0956 |
| | | | | 340/435 |
| 2016/0139755 A1* | 5/2016 | Bushmitch | ................ | H04L 9/32 |
| | | | | 715/707 |

FOREIGN PATENT DOCUMENTS

| | | |
|---|---|---|
| CN | 204264138 U | 4/2015 |
| CN | 105303828 A | 2/2016 |
| JP | 2008-203915 A | 9/2008 |

OTHER PUBLICATIONS

Office Action dated Apr. 26, 2017 issued in corresponding Chinese Application No. 201510566254.4.
Office Action dated Jun. 16, 2017 issued in corresponding Chinese Application No. 201510566254.4.

* cited by examiner

METHOD FOR DETERMINING TARGET OF ALCOHOL TEST, DRIVING SAFETY DEVICE AND SYSTEM, SERVER

This is a National Phase Application filed under 35 U.S.C. 371 as a national stage of PCT/CN2016/077635, filed Mar. 29, 2016, an application claiming the benefit of Chinese Application No. 201510566254.4, filed Sep. 8, 2015, the content of each of which is hereby incorporated by reference in its entirety.

TECHNICAL FIELD

The present invention relates to the field of driving safety, and particularly relates to a method for determining a target of alcohol test, a driving safety device for performing the method, a server used cooperatively with the driving safety device, and a driving safety system including the driving safety device and the server.

BACKGROUND

At present, drunk driving is one of important factors leading to traffic accidents. Generally, a method for detecting the drunk driving, in which vehicles are stopped and checked at checkpoints located at fixed locations, is used. The method, however, has at least the following two disadvantages. First, the detection method has a certain degree of randomness and can be performed only at specific road sections. Second, when a vehicle driven by a drunk driver has not passed any checkpoint, there is still a huge risk of road safety.

Therefore, how to accurately determine a drunk driver has become an urgent technical problem to be solved in the filed.

SUMMARY

An object of the present invention is to provide a method for determining a target of alcohol test, a driving safety device for performing the method, a server used cooperatively with the driving safety device, and a driving safety system including the driving safety device and the server. Drunk drivers can be accurately and comprehensively identified by using the driving safety system.

According to an aspect of the present invention, there is provided a method for determining a target of alcohol test, including: determining whether a motor vehicle satisfies a preset condition; and determining, as a target vehicle, a motor vehicle that satisfies at least one preset condition. The preset condition includes at least one of the following conditions: Condition 1, a parking duration in an area, in which a distance from a place selling alcoholic drinks does not exceed a predetermined distance, has a value within a predetermined range; Condition 2, alcohol content in a body of a driver of the motor vehicle exceeds a predetermined value; and Condition 3, schedule of a driver of the motor vehicle on that driving day includes having a meal and/or a dinner party.

According to an embodiment of the present invention, the predetermined range may be a range from 0.5 hour to 6 hours.

According to an embodiment of the present invention, the predetermined distance may be ranged from 100 meters to 200 meters.

According to an embodiment of the present invention, in a case where the preset condition includes Condition 2, the step of determining whether a motor vehicle satisfies a preset condition may further include: irradiating, by using infrared rays, the driver of the motor vehicle; and determining whether an amount of the infrared rays absorbed by the driver exceeds a predetermined value. It is determined that the preset condition is satisfied if the amount exceeds the predetermined value.

According to an embodiment of the present invention, in a case where the preset condition includes Condition 3, the method may further include acquiring information on the schedule of the driver of the motor vehicle.

According to an embodiment of the present invention, the method for determining a target of alcohol test may further include acquiring information on all motor vehicles being driven within a predetermined area.

According to an embodiment of the present invention, in a case where the preset condition includes Condition 1, the method for determining a target of alcohol test may further include: acquiring information on a business place around the parking place of the motor vehicle, and determining whether the business place includes a place selling alcohol drinks.

According to another aspect of the present invention, there is provided a driving safety device including a condition determination module, a first control module and a first communication module. The condition determination module is configured for determining whether a motor vehicle equipped with the driving safety device satisfies a preset condition, and for transmitting a warning signal to the first control module when the condition determination module has determined that the motor vehicle equipped with the driving safety device satisfies the preset condition. The preset condition includes at least one of the following conditions: Condition 1, a parking duration has a value within a predetermined range; Condition 2, alcohol content in a body of a driver of the motor vehicle exceeds a predetermined value; and Condition 3, schedule of a driver of the motor vehicle on that driving day includes having a meal and/or a dinner party. Upon receipt of the warning signal, the first control module transmits a first executing signal to the first communication module. Upon receipt of the first executing signal, the first communication module transmits information on the motor vehicle equipped with the driving safety device to a remote server.

According to an embodiment of the present invention, the predetermined range may be a range from 0.5 hour to 6 hours.

According to an embodiment of the present invention, the driving safety device may further include an infrared-ray emitting module configured for emitting infrared rays for irradiating the driver of the motor vehicle; and an infrared-ray absorption amount detection module configured for detecting an amount of the infrared rays absorbed by the driver of the motor vehicle, and for transmitting the absorbed amount to the condition determination module. The condition determination module transmits the warning signal when the absorbed amount exceeds a predetermined value.

According to an embodiment of the present invention, the condition determination module may acquire information on schedule of a driver through the first communication module.

According to an embodiment of the present invention, the driving safety device may further include a positioning module configured for determining position information of the motor vehicle, and the information on the motor vehicle may include the position information and a license number of the motor vehicle.

According to an embodiment of the present invention, the driving safety device may further include an alerting module capable of transmitting an alert signal upon receipt of a second executing signal, which is transmitted by the first control module after the first control module receives the warning signal.

According to another aspect of the present invention, there is provided a server including a second control module, a second communication module and a storage module. The storage module stores therein a map and a database of a predetermined area. The second control module is configured for receiving information on vehicle acquired by the second communication module, and for comparing the information on vehicle with information stored in the database to identify, as a target vehicle, a motor vehicle that satisfies a preset condition. The preset condition includes at least one of the following conditions: Condition 1, a parking duration has a value within a predetermined range; Condition 2, alcohol content in a body of a driver of the motor vehicle exceeds a predetermined value; and Condition 3, schedule of a driver of the motor vehicle on that driving day includes having a meal and/or a dinner party. In a case where the preset condition includes at least one of Condition 2 and Condition 3, the second control module identifies, as the target vehicle, a motor vehicle that satisfies the preset condition. In a case where the preset condition includes Condition 1, the second control module marks, on the map, all places selling alcohol drinks within a predetermined area, compares the position of the motor vehicle with the places selling alcohol drinks, and identifies the motor vehicle as the target vehicle if the position of the motor vehicle has a distance from any of the places selling alcohol drinks that is no greater than a predetermined distance.

According to an embodiment of the present invention, the predetermined distance may be ranged from 100 meters to 200 meters.

According to another aspect of the present invention, there is provided a driving safety system including the driving safety device and the server according embodiments of to the present invention. The second communication module of the server is in communication with the first communication module of the driving safety device.

According to the method for determining a target of alcohol test provided by embodiments of the present invention, it is possible to identify, as a target vehicle, a motor vehicle that satisfies at least one preset condition, to locate the specific position of the target vehicle, go to the position of the target vehicle, and check the target vehicle. In this way, the checking on drunk driving can be more purposive such that efficiency thereof is improved, and accuracy of the checking on drunk driving can be improved and the missing probability can be reduced, such that the traffic safety is improved.

BRIEF DESCRIPTION OF THE FIGURES

The accompanying drawings, which constitute a part of the specification, are provided for further understanding of the present invention, and for explaining the present invention together with the following specific implementations, but not intended to limit the present invention. In the drawings.

DETAILED DESCRIPTION OF THE EMBODIMENTS

Figure 1:
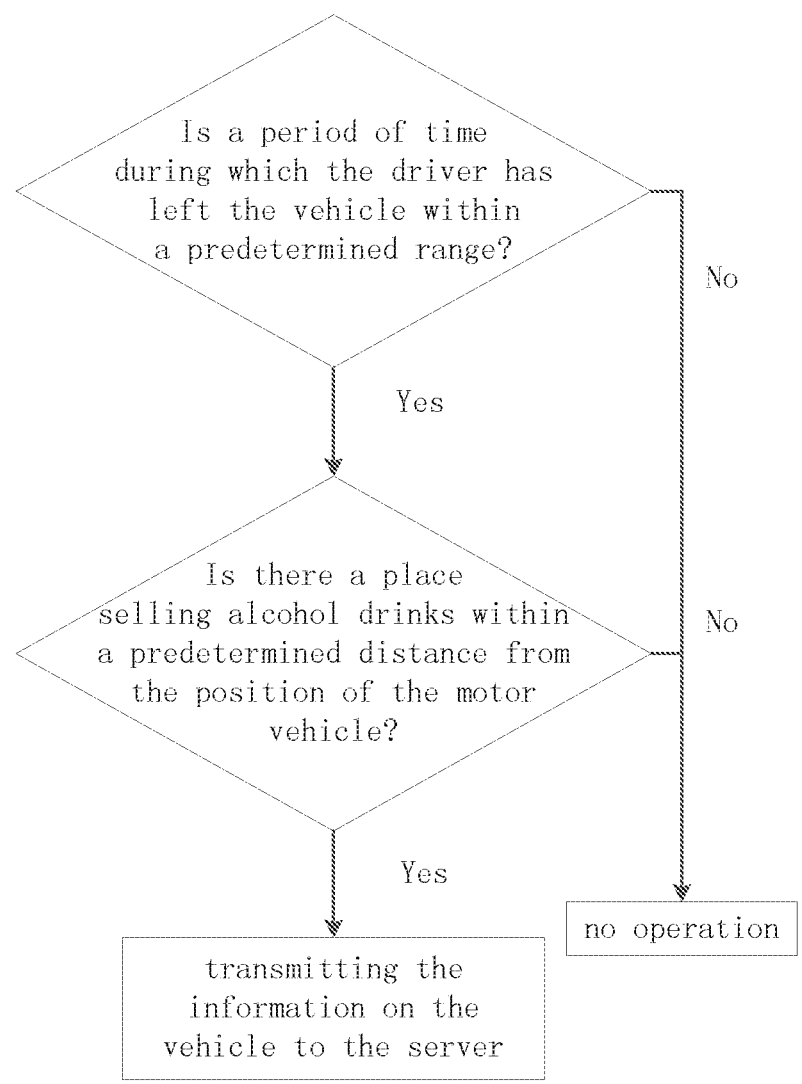
FIG. 1 is a flowchart of a method for determining a target of alcohol test according to an embodiment of the present invention.

Specific embodiments of the present invention will be described below in detail in conjunction with the accompanying drawings. It should be understood that the embodiments to be described herein are only intended to illustrate and explain the present invention, but not to limit the present invention.

According to an embodiment of the present invention, there is provided a method for determining a target of alcohol test, and the method includes: determining whether a motor vehicle satisfies a preset condition; and determining, as a target vehicle, a motor vehicle that satisfies at least one preset condition.

The preset condition includes at least one of the following conditions: Condition 1, a parking duration in an area, in which a distance from a place selling alcoholic drinks does not exceed a predetermined distance, has a value within a predetermined range; Condition 2, alcohol content in a body of a driver of the motor vehicle exceeds a predetermined value; and Condition 3, schedule of a driver of the motor vehicle on that driving day includes having a meal and/or a dinner party.

In a case where the parking duration of a motor vehicle in an area around a place selling alcohol drinks has a value within a predetermined range (e.g., the predetermined range may be a range from 0.5 hour to 6 hours), it indicates that it is highly possible for the driver of the motor vehicle to have drunk an alcohol drink in the place and then to drive on. It will be more purposive if the test or checking is performed on the driver of the motor vehicle who satisfies this preset, and the missing of checking can be avoided.

In this embodiment, the predetermined range may be a range from 0.5 hour to 6 hours. In a case where the parking duration of a motor vehicle in an area around a place selling alcohol drinks is less than 0.5 hour, it indicates that it is barely possible for the driver of the motor vehicle to have drunk an alcohol drink. In a case where the parking duration of a vehicle in an area around a place selling alcohol drinks exceeds 6 hours, it indicates that it is highly possible for the driver of the motor vehicle to be a resident around the place selling alcohol drinks. In other cases, even if the driver of the motor vehicle has drunk alcohol drinks, the alcohol is metabolized out of the body of the driver after the driver's staving over 6 hours, and there is almost no risk of drunk driving. However, in a case where the parking duration of a motor vehicle in an area around a place selling alcohol drinks is between 0.5 hour and 6 hours, it indicates that it is highly possible for the driver of the motor vehicle to have drunk and then to drive on. For example, in a case where the parking duration of a motor vehicle in an area around a place selling alcohol drinks is 1 hour, it indicates that it is highly possible for the driver of the motor vehicle to have drunk alcohol drinks within the 1 hour of staving.

A place selling alcohol drinks may be a pub, a restaurant or the like, and there is no particularly limitation on the predetermined distance. For example, the predetermined distance may be ranged from 100 meters to 200 meters. The specific values of the predetermined distance may be set according to the specific conditions of the area where the method is implemented.

In a case where the alcohol content in the body of a driver of a motor vehicle exceeds a predetermined value, it indicates that the driver of the motor vehicle is in a drunk-driving state. By identifying the motor vehicle as the target vehicle and checking the motor vehicle, an occurrence of accident can be avoided.

In a case where the schedule of a driver of a motor vehicle on that driving day includes having a meal and/or a dinner party, it is highly possible for the driver of the motor vehicle to drink alcohol drinks on that day. It will be more purposive if the checking is performed on the driver of the motor vehicle who satisfies this condition, and the missing of checking can be avoided.

Immediately after a motor vehicle that satisfies at least one of above conditions is identified as a target vehicle, the specific position of the target vehicle can be located. One can go to the position of the target vehicle, and check the target vehicle. In this way, the checking on drunk driving can be more purposive such that efficiency thereof is improved, and accuracy of the checking can be improved and the missing probability can be reduced, such that the traffic safety is improved.

According to an embodiment of the present invention, the step of determining whether alcohol content in a body of a driver of the motor vehicle exceeds a predetermined value may include: irradiating, by using infrared rays, a driver of the motor vehicle; and determining whether an amount of the infrared rays absorbed by the driver of the motor vehicle exceeds a predetermined value. It is determined that alcohol content in a body of a driver of the motor vehicle exceeds a predetermined value if the absorbed amount exceeds the predetermined value.

The infrared rays for irradiating the driver of the motor vehicle may be emitted from an infrared-ray emitting device mounted in the cab. In addition, a result from the determination may be transmitted to a traffic management department.

According to an embodiment of the present invention, whether schedule of a driver of the motor vehicle on that driving day includes having a meal and/or a dinner party can be determined by acquiring information on the schedule of the driver of the motor vehicle.

The information on the schedule of the driver may be set in a vehicle electronic equipment, or may be set in a smart phone of the driver. In a case where the information on the schedule of the driver of the motor vehicle has been acquired, it is possible to identify the information on the schedule, and determine whether the information on the schedule includes information on having a meal and/or a dinner party, and the like. If such the information is included, it indicates that it is highly possible for the driver to drink alcohol drinks on that day.

According to an embodiment of the present invention, information on all motor vehicles within a predetermined area may be acquired. The predetermined area may be an area managed by a traffic management department. In a case where information on all motor vehicles being driven within the predetermined area has been acquired, it is possible to facilitate the management of the vehicles within the area managed by a traffic police.

According to an embodiment of the present invention, information on a business place around the parking place of the motor vehicle can be acquired, and whether the business place includes a place selling alcohol drinks can be determined.

Figure 2:
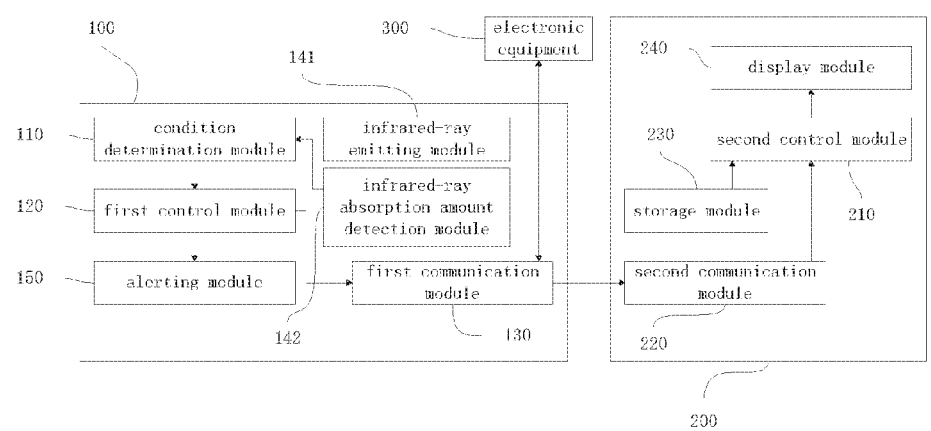
FIG. 2 is a block diagram of a driving safety system according to an embodiment of the present invention.

According to another aspect of the present invention, there is provided a driving safety device 100, as shown in FIG. 2. The driving safety device 100 may include a condition determination module 110, a first control module 120 and a first communication module 130.

The condition determination module 110 is configured for determining whether a motor vehicle equipped with the driving safety device 100 satisfies a preset condition. A warning signal is transmitted to the first control module 120 by the condition determination module 110 when it has determined that the motor vehicle equipped with the driving safety device 100 satisfies the preset condition. The preset condition includes at least one of the following conditions: Condition 1, a parking duration has a value within a predetermined range; Condition 2, alcohol content in a body of a driver of the motor vehicle exceeds a predetermined value; and Condition 3, schedule of a driver of the motor vehicle on that driving day includes having a meal and/or a dinner party.

Upon receipt of the warning signal, the first control module 120 transmits a first executing signal to the first communication module 130. Upon receipt of the first executing signal, the first communication module 130 transmits information on the motor vehicle equipped with the driving safety device 100 to a remote server 200.

The driving safety device 100 may be mounted in the motor vehicle, and the information on the motor vehicle may include the position, the license number and the like of the motor vehicle.

In a case where a parking duration of a motor vehicle has a value exceeding the predetermined range and the motor vehicle starts to move again, the condition determination module 110 may determine that the motor vehicle satisfies the preset condition, and may transmit information on the motor vehicle equipped with the driving safety device 100 to a remote server 200 via the first communication module 130.

As shown in FIG. 2, the server 200 may include a second control module 210, a second communication module 220 and a storage module 230. The second communication module 220 is configured for communicating with the first communication module 130 of the driving safety device 100. The storage module 230 stores therein a map and a database of a predetermined area. The second control module 210 receives the information on vehicle acquired by the second communication module 220, and compares the information on vehicle with information stored in the database to identify, as a target vehicle, the motor vehicle that satisfies the preset condition.

According to an embodiment of the present invention, the driving safety device 100 may include an infrared-ray emitting module 141 and an infrared-ray absorption amount detection module 142, in order to determine whether alcohol content in the body of the driver of the motor vehicle exceeds the predetermined value. The infrared-ray emitting module 141 is configured for emitting infrared rays for irradiating a driver of the motor vehicle. The infrared-ray absorption amount detection module 142 is configured for detecting an amount of the infrared rays absorbed by the driver, and for transmitting the absorbed amount to the condition determination module 110. The condition determination module 110 transmits the warning signal when the absorbed amount exceeds a predetermined value.

After a person has drunk alcohol drinks, alcohol will enter human tissues. Compared with one without drinking, tissues of a drinker are capable of absorbing more light rays. Normal driving of drivers will not be interrupted by the detection of the alcohol content of the bodies of the drivers with the infrared-ray emitting module 141 and the infrared-ray absorption amount detection module 142, thereby not only achieving high accuracy of checking but also high driving safety.

According to an embodiment of the present invention, information on schedule of a driver may be acquired by the first control module 120 via the first communication module 130. For example, the information on schedule of a driver may be acquired from an electronic equipment 300, in which the information on schedule of the driver is stored, by the first control module 120 via the first communication module 130. The electronic equipment 300 may be a cell phone of the driver, or other vehicle electronic equipment. The condition determination module 100 may search for a keyword such as "dinner party", "meal", or "drinking" from the acquired information on schedule. If such keyword exists, it can be determined that the motor vehicle satisfies the preset condition of "schedule of a driver of the motor vehicle on that driving day includes having a meal and/or a dinner party", and the warning signal may be generated.

According to an embodiment of the present invention, the driving safety device 100 may include a positioning module capable of determining the position of the motor vehicle. In addition, the driving safety device 100 may further include a storage module for storing information on vehicle such as a license number of the motor vehicle.

According to an embodiment of the present invention, the driving safety device 100 may further include an alerting module 150. Upon receipt of the warning signal, the first control module 120 may transmit a second executing signal to the alerting module 150, and the alerting module 150 transmits an alert signal after receiving the second executing signal. Through the alert signal transmitted by the warning module 150, it is possible to notice that it is possible for the driver to be in a state of drunk driving.

The second control module 210 of the server 200 receives the information on vehicle acquired by the second communication module 220, and compares the information on vehicle with information stored in the database to identify, as a target vehicle, a motor vehicle that satisfies a preset condition. In a case where the preset condition includes at least one of a condition that alcohol content in the body of a driver of the motor vehicle exceeds a predetermined value and a condition that schedule of a driver of the motor vehicle on that driving day includes having a meal and/or a dinner party, the second control module 210 of the server 200 may identifies, as the target vehicle, the motor vehicle that satisfies the preset condition.

In a case where the preset condition includes a condition that a parking duration has a value within a predetermined range, the second control module 210 marks, on the map, all places selling alcohol drinks within a predetermined area, compares the position of the motor vehicle with the places selling alcohol drinks, and identifies the motor vehicle as the target vehicle if the position of the motor vehicle has a distance from any of the places selling alcohol drinks that is no greater than a predetermined distance.

The information on the motor vehicle on which a drunk driving is possibly occurred is acquired by the second communication module 220, such that the traffic police can arrive at the position of the motor vehicle quickly and check the motor vehicle, thereby the occurrence of drunk driving is avoided.

According to an embodiment of the present invention, the server 200 may further include a display module 240 for displaying information on the target vehicle.

As another aspect of the present invention, there is provided a driving safety system including the driving safety device 100 and the server 200 according to embodiments of the present invention.

Steps of an example method for determining a target of alcohol test executed by using the driving safety system provided by embodiments of the present invention will be described below with reference to FIG. 1. In the example method shown in FIG. 1, the preset condition is that a parking duration in an area, in which a distance from a place selling alcoholic drinks does not exceed a predetermined distance, has a value within a predetermined range. The predetermined range is a range from 0.5 hour to 6 hours, and the predetermined distance is 100 meters.

Referring to FIG. 1, when a vehicle is started again after being parked over a period of time, whether a period of time during which the driver has left the vehicle is within a predetermined range (i.e., whether the period of time is within 0.5 hour to 6 hours is determined. When the result from the determination is "YES", the information on the vehicle is transmitted to the server, and the server determines whether there is a place selling alcohol drinks such as a restaurant or a pub within a predetermined distance (e.g., 100 meters) from the position of the motor vehicle. If any of the results from the above two determinations is "NO", no operation will be performed. If both of the results from the above two determinations are "YES", information on the vehicle is transmitted to the server, and the nearby traffic police is notified of performing a check on the motor vehicle.

It can be understood that the foregoing implementations are merely exemplary implementations used for describing the principle of the present invention, but the present invention is not limited thereto. Those of ordinary skill in the art may make various variations and improvements without departing from the spirit and essence of the present invention, and these variations and improvements shall fall into the protection scope of the present invention.

What is claimed is:

1. A method for determining a target of alcohol test, comprising:
   acquiring, by a condition determination module of a driving safety device, information on a schedule of a driver through a first communication module of the driving safety device;
   determining, by the condition determination module, whether a motor vehicle satisfies a preset condition; and
   determining, by a second control module of a server, as a target vehicle, a motor vehicle that satisfies at least one preset condition, wherein
   the preset condition comprises at least one of the following conditions:
   Condition 1, a parking duration in an area, in which a distance from a place selling alcoholic drinks does not exceed a predetermined distance, has a value within a predetermined range;
   Condition 2, alcohol content in a body of a driver of the motor vehicle exceeds a predetermined value; and
   Condition 3, schedule of the driver of the motor vehicle on that driving day comprises having a meal and/or a dinner party.

2. The method according to claim 1, wherein the predetermined range is a range from 0.5 hour to 6 hours.

3. The method according to claim 1, wherein the predetermined distance is ranged from 100 meters to 200 meters.

4. The method according to claim 1, wherein in a case where the preset condition comprises Condition 2, the step of determining whether the motor vehicle satisfies the preset condition further comprise:
- irradiating, by using infrared rays, the driver of the motor vehicle; and
- determining whether an amount of the infrared rays absorbed by the driver of the motor vehicle exceeds a predetermined value,
- wherein it is determined that the preset condition is satisfied if the amount exceeds the predetermined value.

5. The method according to claim 1, wherein in a case where the preset condition comprises Condition 1, the method further comprises:
- acquiring, by the second control module, information on a business place around a parking place of the vehicle, and
- determining, by the second control module, whether the business place comprises a place selling alcohol drinks.

6. A driving safety device, comprising a condition determination module, a first control module and a first communication module, wherein
- the condition determination module is configured to determine whether a motor vehicle equipped with the driving safety device satisfies a preset condition, and transmit a warning signal to the first control module when the condition determination module has determined that the motor vehicle equipped with the driving safety device satisfies the preset condition, the preset condition comprises at least one of the following conditions:
- Condition 1, a parking duration has a value within a predetermined range;
- Condition 2, alcohol content in a body of a driver of the motor vehicle exceeds a predetermined value; and
- Condition 3, schedule of the driver of the motor vehicle on that driving day includes having a meal and/or a dinner party,
- upon receipt of the warning signal, the first control module transmits a first executing signal to the first communication module, and
- upon receipt of the first executing signal, the first communication module transmits information on the motor vehicle equipped with the driving safety device to a remote server,
- wherein the condition determination module acquires information on a schedule of the driver through the first communication module.

7. The driving safety device according to claim 6, wherein the predetermined range is a range from 0.5 hour to 6 hours.

8. The driving safety device according to claim 6, further comprising:
- an infrared-ray emitting module configured to emit infrared rays for irradiating the driver of the motor vehicle; and
- an infrared-ray absorption amount detection module configured to detect an amount of the infrared rays absorbed by the driver of the motor vehicle, and transmit the absorbed amount to the condition determination module,
- wherein the condition determination module transmits the warning signal when the absorbed amount exceeds a predetermined value.

9. The driving safety device according to claim 6, further comprising a positioning module configured to determine position information of the motor vehicle, and the information on the motor vehicle includes the position information and a license number of the motor vehicle.

10. The driving safety device according to claim 6, further comprising an alerting module capable of transmitting an alert signal upon receipt of a second executing signal, the second executing signal being transmitted by the first control module after the first control module receives the warning signal.

11. A server, comprising a second control module, a second communication module and a storage module, wherein
- the storage module stores therein a map and a database of a predetermined area,
- the second control module is configured to receive information on vehicle acquired by the second communication module, and compare the information on vehicle with information stored in the database to identify, as a target vehicle, a motor vehicle that satisfies a preset condition,
- the preset condition comprises at least one of the following conditions:
- Condition 1, a parking duration has a value within a predetermined range;
- Condition 2, alcohol content in a body of a driver of the motor vehicle exceeds a predetermined value; and
- Condition 3, schedule of a driver of the motor vehicle on that driving day includes having a meal and/or a dinner party,
- wherein in a case where the preset condition comprises at least one of Condition 2 and Condition 3, the second control module identifies, as the target vehicle, a motor vehicle that satisfies the preset condition,
- in a case where the preset condition comprises Condition 1, the second control module marks, on the map, all places selling alcohol drinks within a predetermined area, compares the position of the motor vehicle with the places selling alcohol drinks, and identifies the motor vehicle as the target vehicle if the position of the motor vehicle has a distance from any of the places selling alcohol drinks that is no greater than a predetermined distance,
- wherein the second communication module of the server is in communication with the first communication module of the driving safety device according to claim 6.

12. The server according to claim 11, wherein the predetermined distance is ranged from 100 meters to 200 meters.

13. A driving safety system, comprising the driving safety device according to claim 6 and a server comprising a second control module, a second communication module and a storage module, wherein
- the storage module of the server stores therein a map and a database of a predetermined area,
- the second control module of the server is configured to receive information on vehicle acquired by the second communication module, and compare the information on vehicle with information stored in the database to identify, as a target vehicle, a motor vehicle that satisfies the preset condition,
- wherein in a case where the preset condition comprises at least one of Condition 2 and Condition 3, the second control module of the server identifies, as the target vehicle, a motor vehicle that satisfies the preset condition,
- in a case where the preset condition comprises Condition 1, the second control module of the server marks, on the map, all places selling alcohol drinks within a predetermined area, compares the position of the motor vehicle with the places selling alcohol drinks, and identifies the motor vehicle as the target vehicle if the position of the motor vehicle has a distance from any of the places selling alcohol drinks that is no greater than a predetermined distance, and wherein the second communication module of the server is in communication with the first communication module of the driving safety device.

14. The driving safety system according to claim 13, wherein the predetermined distance is ranged from 100 meters to 200 meters.

\* \* \* \* \*